United States Patent [19]

America

[11] Patent Number: 4,876,005
[45] Date of Patent: Oct. 24, 1989

[54] HIGH PRESSURE COLUMN ASSEMBLY FOR A LIQUID CHROMATOGRAPH SYSTEM

[75] Inventor: William G. America, Danbury, Conn.

[73] Assignee: The Perkin-Elmer Corporation, Norwalk, Conn.

[21] Appl. No.: 281,374

[22] Filed: Dec. 8, 1988

Related U.S. Application Data

[63] Continuation of Ser. No. 155,394, Feb. 12, 1988, abandoned.

[51] Int. Cl.⁴ .............................................. B01D 15/08
[52] U.S. Cl. ..................................... 210/198.2; 55/386
[58] Field of Search ............ 210/635, 656, 659, 198.2; 55/386

[56] References Cited

U.S. PATENT DOCUMENTS

| | | | |
|---|---|---|---|
| 3,250,395 | 5/1966 | Blume | 210/198.2 |
| 3,615,235 | 10/1971 | Harding | 210/198.2 |
| 3,682,315 | 8/1972 | Haller | 210/198.2 |
| 3,855,130 | 12/1974 | Randau | 210/198.2 |
| 3,904,527 | 9/1975 | Wilhelmson | 210/198.2 |
| 4,313,828 | 2/1982 | Brown | 210/198.2 |
| 4,451,364 | 5/1984 | Higgins | 210/198.2 |
| 4,563,275 | 1/1986 | McEachern | 210/198.2 |
| 4,578,193 | 3/1986 | Shephard | 210/198.2 |
| 4,655,917 | 4/1987 | Shackelford | 210/198.2 |
| 4,747,284 | 4/1988 | Hauke | 210/198.2 |

Primary Examiner—Ernest G. Therkorn
Attorney, Agent, or Firm—Edwin T. Grimes

[57] ABSTRACT

Liquid chromatography column coupling assembly having a column enclosed in a housing member to form a column cartridge and including coupling assemblies at respective ends of the cartridge, each comprising a coupler member and a collar member. The coupler member and collar member are tubular in configuration and disposed in coaxial telescoping relation with one end of the coupler member abutting the respective end of the column with an annular seal interposed therebetween. The collar member has one end threaded onto the end of the column housing and at its opposite end an inwardly extending radial flange coacting with an outwardly extending radial flange on said one end of the coupling member. Rotation of the collar member when threading it onto the column housing causes relative axial displacement of the members to compress the seal between the abutting ends of the column and coupler member.

9 Claims, 1 Drawing Sheet

U.S. Patent   Oct. 24, 1989   4,876,005
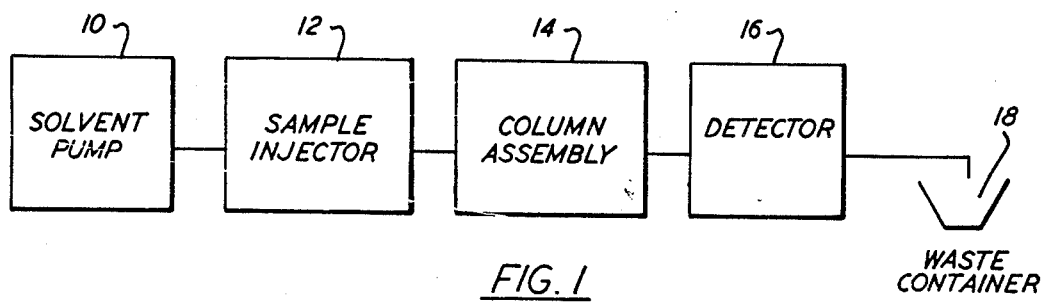
FIG. 1
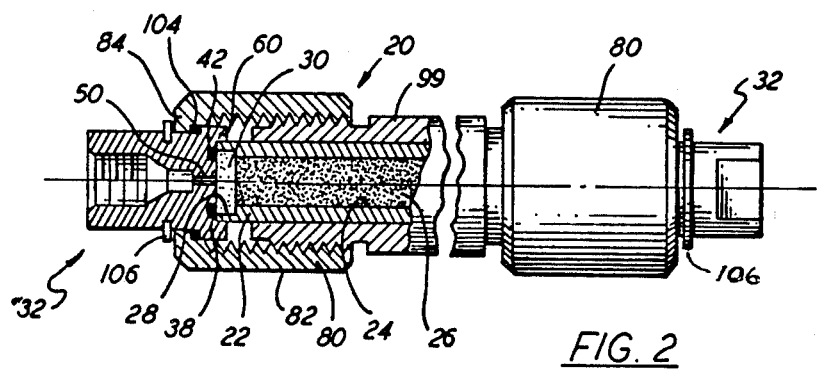
FIG. 2
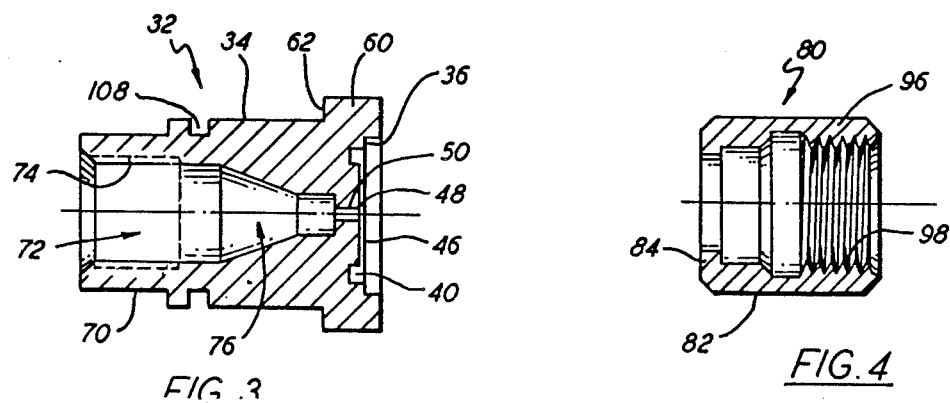
FIG. 3
FIG. 4
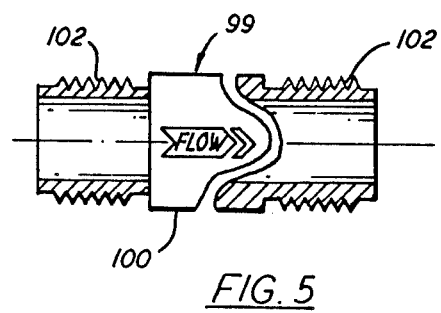
FIG. 5

HIGH PRESSURE COLUMN ASSEMBLY FOR A LIQUID CHROMATOGRAPH SYSTEM

This application is a continuation of application Ser. No. 07/155,394 filed Feb. 12, 1988, now abandoned.

The present invention finds application in the field of liquid chromatography and relates to a column assembly coupled between a liquid chromatograph injector and a detector.

BACKGROUND OF THE INVENTION

In the field of liquid chromatography, a liquid (called the "mobile phase") is pumped under high pressure through a separation or partition column, which comprises a tubular member packed with a suitable particulate solid material (the "stationary phase"). As the liquid phase, including a small sample to be separated or assayed, passes through the column the sample components in the liquid phase separate from each other. As the liquid phase elutes from the column, the sample is separated into bands whose concentration is then measured by a suitable detector.

A liquid chromatograph column, in some user situations, may need to be changed frequently. Such column changing may be necessary, for example, in order to permit testing of a sample with a column having a different stationary phase. Most column changes are made by removing the column from the tubing which couples it to the detector and the sample injector. This usually necessitates the use of wrenches, a fact which in some industrial settings may require the chromatographer to call a maintenance person to perform the column change. Moreover, the use of a wrench or other tool, which is required to tighten the fitting to make it leak proof at typical liquid chromatograph operating pressures of from 6,000 to 10,000 psi, causes wear on the connector nut and ferrule. The cumulative wear eventually causes the fitting to fail under liquid chromatograph operating pressures and require replacement.

In view of the foregoing problems associated with liquid chromatograph column changing, it is an objective of the present invention to provide a new and improved liquid chromatograph column assembly, which will permit changing the column without requiring the use of hand tools.

It is a further objective of the present invention to provide a liquid chromatograph column assembly, which permits the column to be changed without causing significant wear on the sealing gasket member.

BRIEF DESCRIPTION OF THE INVENTION

Briefly, the present invention is directed to a new and improved high pressure column assembly for a liquid chromatograph, which includes a hollow cylindrical column fabricated of liquid impervious material. Stationary phase packing material is disposed within the column and a liquid permeable discoid frit is disposed at each end of the column to retain the packing material and diffuse the flow of mobile phase entering the column.

The column assembly includes a cylindrical housing enveloping the column and is provided with identical couplings at each end. Each coupling assembly includes a tubular coupler member having at one end a radially outwardly extending annular flange. The coupler member is disposed coaxially with respect to the column with the front face of the flange in confronting relation to one end of the column. The front face of the flange contains a concentric annular groove radially positioned to be in apposition to the end of the column and to the outermost circumferential portion of the discoid frit. An annular gasket is disposed in the groove and projects beyond the front face of the flange.

Each coupling assembly also includes a hollow cylindrical collar member having a radially inwardly extending annular flange at one end, disposed in coaxial surrounding relation to the couple member and the housing, the inwardly extending flange of the collar member and outwardly extending flange of the coupler member having radial dimensions such as to place the respective back faces of the flanges in apposition. The inner diameter of the collar member flange is sufficiently large to accommodate passage of the tubular member except for the outwardly extending flange thereof.

The collar member is threadedly coupled to the end of the column husing member whereby rotation of the collar member in one direction relative to the housing member produces axial relative displacement therebetween with concomittant movement of the flanges toward each other and the front face of the coupler member flange toward the column end with consequent compression of the gasket against the column end without substantial rotational displacement of the gasket relative to the column end.

There has thus been outlined rather broadly the more important features of the invention in order that the detailed description thereof that follows may be more readily understood, and in order that the present contribution to the art may be better appreciated. Additional features of the invention will be described more fully hereinafter. Those skilled in the art will appreciate that the conception on which this disclosure is based may readily be utilized as a basis for the design of other assemblies for carrying out the several purposes of the invention. It is important, therefore, that this disclosure be regarded as including such equivalent assemblies as do not depart from the spirit and scope of the invention as defined in the subjoined claims.

One embodiment of the invention has been chosen for purposes of illustration and description, and is shown in the accompanying drawings, forming a part of the specification.

BRIEF DESCRIPTION OF THE DRAWINGS

FIG. 1 is a block diagram of a typical liquid chromatograph which embodies the present invention;

FIG. 2 is an elevational view partially in axial section showing the high pressure column assembly constructed according to the concepts of the invention;

FIG. 3 is an axial sectional view through the coupler member;

FIG. 4 is an axial sectional view through the collar member; and

FIG. 5 is an axial sectional view through the housing member.

DETAILED DESCRIPTION OF THE INVENTION

Referring now to FIG. 1, there is shown in schematic form a typical liquid chromatograph system. In such a typical system, a pump 10, commonly referred to as a solvent delivery pump, is provided for pumping a mobile phase through the system. The mobile phase is first pumped into a sample injector 12 which is utilized to put a fixed volume of an unknown liquid material into the flow of solvent. The solvent and the unknown are then pumped into the liquid chromatograph column assembly 14. The column assembly typically comprises a cylindrical column with appropriate fittings at opposite ends thereof for coupling to the injector 12 and to the detector 16.

The column contains a packing in the form of a solid particulate material appropriate to the substance being analyzed and having different affinities for its various constituents. During the flow of the mobile phase through the column, the time of passage of the individual constituents is retarded by a process of repetitive absorption and desorption by the stationary phase, the length of the delay (the "retention time") being characteristic of and different for each of the constituents. Consequently, the various constituents elute from the column at spaced time intervals and enter the detector 16 which reacts to the presence of the sample constituents in the mobile phase by generating a measurable signal proportional in its intensity to the concentration of the detected constituent. Thus, all in a manner well known in the art, with proper calibration of the instrument, one can determine from the detector output signal the exact mass of the constituent components of the sample injected through the injector and separated by the column 14. After passing through the detector, the solvent and sample are carried to an appropriate waste container as indicated at 18.

In a liquid chromatograph system contemplated by the present invention, the solvent pump typically develops a liquid pressure in the system which is often of the order of many thousands of pounds per square inch. Liquid pressures may in some instances go as high as about 5,000 to about 10,000 pounds per square inch. Under such high liquid pressures, difficulties arise with respect to providing a leak proof system. Consequently, it is not infrequent that column coupling fittings are provided which require the use of hand or power tools in order to produce sufficient sealing pressure between the coupling members to prevent a system leak. This is particularly true with respect to the column end fittings associated with the inlet end of the column as the packing material within the column provides the greatest flow resistance to the flow of the mobile phase through a typical liquid chromatograph as illustrated in FIG. 1; hence the highest pressures in the system are experienced between the pump and the inlet side of the column.

Referring now to FIG. 2, one end of a cylindrical cartridge-type column assembly is illustrated generally at 20. Cartridge column assembly 20 includes a generally cylindrically shaped column 22 containing an axial bore 24 and made of a material which is not corroded by typical liquid chromatography solvents. Disposed within the central bore 24 of column 22 is a particulate packing material 26, the exact nature of which is not germane to the present invention but is well known in the art.

At opposite ends of column 22, the central bore 24 has an enlarged counterbore as illustrated at 28 to provide a recess designed to receive a frit 30 which is press fitted or otherwise secured therein by any suitable mechanical retaining means. Frit 30 retains the particulate matter 26 within the central bore 24 and also diffuses the incoming mobile phase. Frit 30, made of a conventional material, has a greater porosity than does the packing 26. Consequently, liquid passing through the system can pass more easily through frit 30 than it can through packing material 26.

The column coupling assembly includes a generally hollow cylindrical coupler member 32, shown in enlarged detail in FIG. 3. At one end, member 32 has a cylindrical portion 34 carrying a radially outwardly extending coaxial annular flange 60. At the end remote from flange 60, coupler member 32 has a cylindrical portion 70 coaxial with and of smaller diameter than cylindrical portion 34. In operative assembly coupler member 32 is positioned in coaxial abutment with the end of column 22 so that the axis of the cylindrical portion 34 is coincident with the axis of cartridge column 20. The face 36 of flange 60 contains a concentric annular groove 40 in which is disposed an annular gasket member 42 (FIG. 1). Groove 40 is radially dimensioned so that it is in apposition to the end of column 22 and the outermost region of frit 30. As seen in FIG. 2, disposed within the annular groove 40 is a gasket member 42 made of a perfluoroelastomer such as "KAL-REZ NO. 1050" manufactured by Dupont, although a suitable gasket can be made from other similar materials. Alternate types of material should have compression characteristics similar to KAL-REZ NO. 1050 and be chemically inert in the solvents used in liquid chromatography. The gasket 42 is preferably press fitted into the groove 40, although a portion of the gasket 42 when fully inserted into the groove 40 projects out of the groove 40 in a direction facing toward the column 20. In the preferred embodiment of the present invention, for example, groove 40 has a depth of 0.025 inches below face 36 and the gasket has a thickness of 0.030 inches. Accordingly, in its uncompressed state, gasket 42 extends 0.0005 inches to the right, as viewed in FIG. 2, of the face 36 of flange 60 of coupling member 32. This permits column 20 to be pressed in a direction toward the cylindrical portion 34 to thereby compress the gasket 42 and provide a fluid tight seal between the two members at typical liquid chromatography pressures. This sealing of the coupling between the two members is further facilitated by assuring that face 38 of column 22 abuts at least a portion of the adjacent face of gasket 42 when column 22 and cylindrical portion 34 are in their proper abutting relationship as illustrated in FIG. 2.

In the preferred embodiment of the present invention, gasket 42 is made by a die punching process from a sheet of the perfluoroelastomer material which has a thickness substantially identical to that of the desired annular gasket.

Referring again to FIG. 3, the plane of the central face portion 46 of the coupler member 32 is recessed from the plane of the face 36 in its preferred embodiment by from about 0.005 inch to about 0.007 inch. This recess is provided to ensure that a small gap will be formed between central face portion 46 and frit 30 when cartridge column 20 is pressed against coupler member 32 at which time gasket 42 is compressed so that its protrusion beyond face 36 is considerably reduced from its uncompressed state. This small gap forms a chamber or sample distribution cavity 48 between frit 30 and face portion 46, thereby providing a channel for liquid being pumped through the column to pass through between a central bore 50 and frit 30 in a substantially uniform manner. This is particularly advantageous because the liquid being tested thereby enters the packing material of column 20 in a substantially uniform concentration over the entire cross sectional area of the region of the column containing packing 26. A further advantage of having cavity 48 is that frit 30, which acts as a filter in this case, does not as easily become subject to plugging caused by particulate and other foreign matter in the liquid being pumped through the column. By evenly distributing the liquid entering as well as leaving packing 26 over the entire surface of frit 30, the plugging problem is substantially reduced.

Referring now to FIG. 3, coupler member 32, illustrated in axial section, includes the cylindrical portion 34 described in conjunction with FIG. 2. This cylindrical portion 34 is disposed in FIG. 3 to the left of a radially extending flange 60, which has a back face 62. In the final assembly of the fitting according to the present invention, coupler member 32 is arranged to remain substantially rotationally stationary while remaining coupled to a collar member 80, which encircles coupler member 32 in a manner to be described hereinafter in greater detail.

Coupler member 32 includes a second cylindrical portion 70 disposed to the left of cylindrical portion 34, as seen in FIG. 3. Cylindrical portion 70 preferably is provided with two parallel flats suitable for engagement by a wrench, thereby permitting coupler 32 to be tightened onto an externally threaded supply pipe or the like (not shown), which is inserted into internally threaded bore 72. It will be understood that tools may be required for the attachment of coupler member 32 to a supply pipe but not for decoupling and changing the column. While a threaded connection is shown and described, it should be noted that other conventional forms of attachment may be used to couple a pipe to the inner surface of the bore 72.

The inner surface of the bore 72 in the region indicated at 76 gradually tapers inwardly in the direction of end face 46 until it merges with central bore 50. The specific configuration of this portion of the coupler member is not particularly critical and may take any suitable alternative physical design desired. In its preferred form the shape conforms to a 1/16" chemical processing industrial connector and central bore 50 is preferably of a diameter which is approximately the same as the central fluid carrying bore of the inlet or outlet tube which is to be mounted in the coupler member. Bore 50 is of a diameter and a length such as to not adversely affect the chromatographic analysis to be performed.

In the preferred embodiment of the present invention, coupler member 32 is made of a titanium alloy which does not corrode in the presence of typical liquid chromatography solvents. A typical diameter of cylindrical portion 34 of coupler member 32 is 0.300 inches.

Referring now to FIG. 4, collar member 80 of the fitting of the present invention is shown in axial section. Collar member 80 has an outer surface indicated generally at 82, which is suitably grooved or knurled so it may easily be grasped with an operator's hand. Collar member 80 is provided with a radially inwardly extending annular flange 84 which coacts with the mating radially outwardly extending flange 60 to connect coupling member 32 to cartridge column 20, as will be discussed more fully hereinafter. Extending to the right of flange 84, as viewed in FIG. 4, is a cylindrically shaped portion indicated generally at 96, which includes an internally threaded section 98 for coupling to an externally threaded section 102 of housing 99 (FIG. 5), which is adapted to encircle column 22, as best seen in FIG. 2.

Referring to FIG. 5, housing 99 comprises a cylindrical body 100 having external threading 102 at each end for engagement with respective collar members 80. The housing can be made of any suitable material capable of withstanding the mechanical stresses placed thereon and, because it does not come in direct contact with the liquid chromatography solvents, it need not necessarily be made of a material which is corrosion resistant to such solvents.

In a normal assembly operation threaded portions 72 of coupler members 32 are connected to the sample injector and the detector, respectively. One end of the cartridge column housing 99 is connected to one collar member 80 by screw threads 98 and mating screw threads 102. Cartridge column 20 is inserted into the housing and the other collar member is connected to the other end of the housing. Both collar members are rotated until the gaskets 42 engage the frits 30 at the cartridge column ends, respectively. A ring or bushing 104, FIG. 2, is interposed between each flange 84 and corresponding flange 60. The ring has a low coefficient of friction to facilitate the rotational movement between the respective collars 80 and coupler members 32 during assembly. A preferred material for the ring is Delrin.

A high pressure liquid seal is effected by twisting collar members 80 by hand in opposite directions until a strong resistance is felt. After assembly, collar members 80 are locked in position with respect to the associated coupler members 32 by the insertion of a Waldes "E" ring 106, or equivalent, in annular slots 108 (as shown in FIG. 3) provided for the purpose in coupler members 32. Inasmuch as collar members 80 can rotate while coupler members 32 remain rotationally stationary, abrasion between gasket members 42 and the ends of the cartridge column is minimized. It has been found that such hand tightening of the collar members exerts sufficient compression on the gasket as to provide a system which withstands pressures in excess of about 15,000 to about 20,000 pounds per square inch. Further, this new and improved assembly eliminates the necessity of disconnecting either the sample injector or the detector when changing columns. As described, an assembly according to the present invention makes it possible to change columns easily without the use of special tools.

Although a particular embodiment of the invention is herein disclosed for purposes of explanation, further modification thereof, after study of this specification, will be apparent to those skilled in the art to which the invention pertains. Reference should accordingly be had to the appended claims for determining the scope of the invention.

What is claimed is:

1. In combination in a liquid chromatography column assembly including a hollow cylindrical separation column containing a packing material constituting the stationary phase, a liquid permeable discoid frit mounted at each end of the column for retaining the packing material, and a cylindrical housing enveloping the column, a column coupling assembly for each end of said column, comprising:

a tubular coupler member having at one end a concentric radially outwardly extending annular flange disposed coaxially with said column and with the front face of the flange in confronting relation to the end of said column, said front face containing a concentric annular groove radially disposed to be in apposition to the end of said column and the outermost circumferential portion of said discoid frit;

an annular gasket member disposed in said groove and projecting beyond said face of the flange;

a cylindrical collar member having an inwardly extending radial flange at one end, disposed in coaxial relation to said coupler member and said housing, the inwardly extending radial flange of said collar member and outwardly extending annular flange of said coupler member having radial dimensions such as to place the respective back faces of said flanges in apposition, the inner diameter of the collar member flange being sufficient to accommodate passage of said tubular coupler member except for the outwardly extending flange thereof; and means for threadedly coupling said collar member to the end of said housing member, whereby rotation of the collar in one direction relative to the housing member produces axial relative displacement therebetween with concomittant engagement of said apposing flange back faces toward each other and compression of said gasket against the end of said column and circumferential portion of said frit without substantial rotational displacement of said gasket relative to said column end.

2. A column coupling assembly according to claim 1 further comprising a low friction ring interposed between the apposing back faces of said radially outwardly extending annular flange on said coupler member and said radially inwardly extending annular flange on said collar member.

3. The assembly according to claim 2 further comprising means for locking said collar member in operative position with respect to said coupler member.

4. The assembly according to claim 3 wherein said means for locking comprises an "E" ring positioned in an annular slot.

5. The assembly of claim 1 wherein said coupler member faces have centrally recessed portions for forming sample distribution cavities adjacent said frit respectively to allow samples to be radially evenly distributed.

6. The assembly according to claim 5 wherein said recess is between about 0.005 inches and about 0.007 inches.

7. A column coupling assembly according to claim 1 wherein said threadedly coupling means includes a threaded portion at an end of said cylindrical housing.

8. The assembly according to claim 7 wherein said threadedly coupling means further include a threaded portion on said collar member which mates with the threaded portion on the cylindrical housing.

9. The assembly according to claim 1 wherein said gasket member is fabricated from a perflouroelastomer.

* * * * *